US00PP24598P2

(12) United States Plant Patent
Bauer

(10) Patent No.: US PP24,598 P2
(45) Date of Patent: Jul. 1, 2014

(54) ***COREOPSIS* 'BROAD STREET'**

(50) Latin Name: *Coreopsis verticillata*
Varietal Denomination: Broad Street

(71) Applicant: Patricia M. Bauer, Lucinda, PA (US)

(72) Inventor: Patricia M. Bauer, Lucinda, PA (US)

(73) Assignee: Itsaul Plants LLC, Alpharetta, GA (US)

( * ) Notice: Subject to any disclaimer, the term of this patent is extended or adjusted under 35 U.S.C. 154(b) by 6 days.

(21) Appl. No.: 13/573,632

(22) Filed: Sep. 27, 2012

(51) Int. Cl.
*A01H 5/00* (2006.01)

(52) U.S. Cl.
USPC ..... Plt./417

(58) Field of Classification Search
USPC ..... Plt./417
See application file for complete search history.

*Primary Examiner* — Annette Para
(74) *Attorney, Agent, or Firm* — Penny J. Aguirre

(57) ABSTRACT

A new cultivar of *Coreopsis verticillata* named 'Broad Street' characterized by its ray florets that are red in color on the upper surface with flecks of yellow primarily appearing on the tips when mature and greyed-yellow and suffused at base with red on the lower surface, its *C. verticillata* type foliage, its cold hardiness to at least U.S.D.A. Zone 5, its continuous blooms from late May/early June until frost, its height of 45 to 60 cm and an average spread of 45 cm, and its vigorous growth habit and ability to propagate well under greenhouse conditions in winter.

2 Drawing Sheets

Botanical classification: *Coreopsis verticillata.*
Variety denomination: 'Broad Street'.

BACKGROUND OF THE INVENTION

The present invention relates to a new and distinct cultivar of *Coreopsis* plant, botanically known as *Coreopsis verticillata* 'Broad Street' and will be referred to hereinafter by its cultivar name, 'Broad Street'. The new cultivar of *Coreopsis* is an herbaceous perennial grown for landscape and container use.

The new invention arose as a naturally occurring whole plant mutation in the Inventor's garden in Lucinda, Pa. in summer of 2009. The parent plants of 'Broad Street' are unknown.

Asexual reproduction of the new cultivar was first accomplished by stem tip cuttings under the direction of the Inventor in Alpharetta, Ga. in October of 2010. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Broad Street' as unique from all *Coreopsis* cultivars known to the Inventor.

1. 'Broad Street' exhibits ray florets that are red in color on the upper surface with flecks of yellow appearing primarily on the tips when mature and greyed-yellow and suffused at base with red on the lower surface.
2. 'Broad Street' exhibits *C. verticillata* type foliage.
3. 'Broad Street' has shown to be hardy at least in U.S.D.A. Zone 5.
4. 'Broad Street' blooms continuously from late May/early June until frost in Pennsylvania without deadheading.
5. 'Broad Street' exhibits a height of 45 to 60 cm (18 to 24 inches) and an average spread of 45 cm (18 inches).

6. 'Broad Street' exhibits a vigorous growth habit and propagates well under greenhouse conditions in winter.

'Broad Street' can be most closely compared to *Coreopsis* 'Route 66' (U.S. Plant Pat. No. 20,609) and *Coreopsis* 'Limerock Ruby' (U.S. Plant Pat. No. 15,455). 'Route 66' is similar to 'Broad Street' in being easily propagated over winter and in having a long blooming habit. 'Route 66' differs from 'Broad Street' in having ray florets that are yellow in color with a prominent eye and becoming almost solid burgundy when they mature, and in being 4 to 6 inches taller in height. 'Limerock Ruby' is similar to 'Broad Street' in having ray florets that are red toned in color and in having *C. verticillata* type foliage. 'Limerock Ruby' differs from 'Broad Street' in having ray florets that are more red-purple in color with flecks of white rather than yellow on the upper surface, in being hardy only to U.S.D.A. Zone 8, and in being shorter in height.

BRIEF DESCRIPTION OF THE DRAWING

The accompanying colored photographs illustrate the overall appearance and distinct characteristics of the new *Coreopsis* as grown in Alpharetta, Ga. The photographs were taken of plants about one year in age as grown in a 2-gallon container without deadheading.

The photograph in FIG. 1 provides a side view of 'Broad Street' in bloom.

Figure 1:
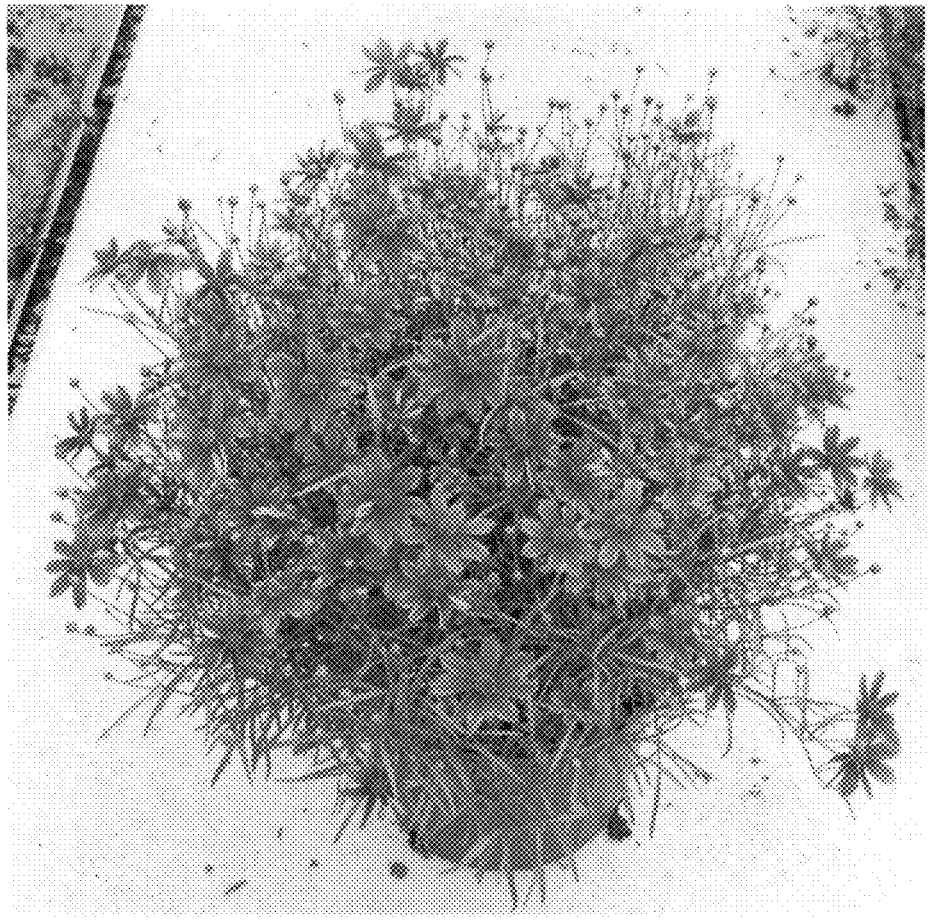
Figure 2:
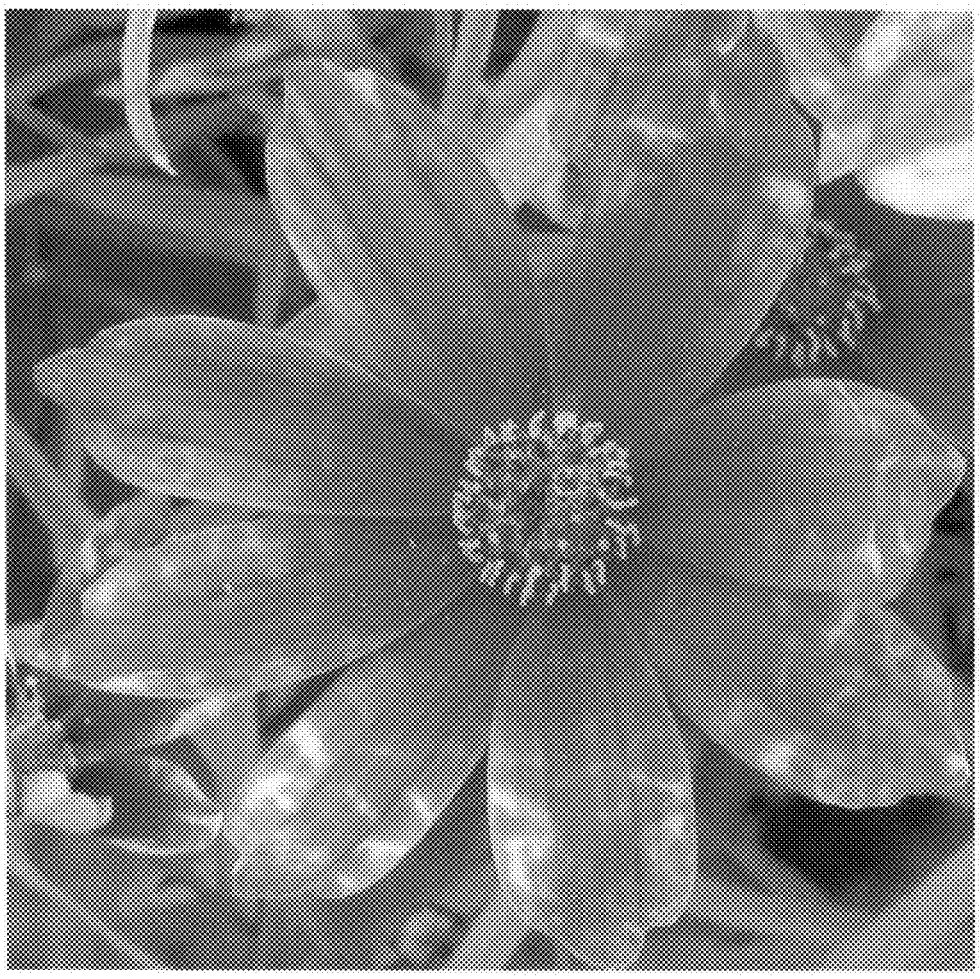

The photograph in FIG. 2 provides a close-up view of an inflorescence of 'Broad Street'. The colors in the photographs may differ slightly from the color values cited in the detailed botanical description, which accurately describe the colors of the new *Coreopsis.*

DETAILED BOTANICAL DESCRIPTION

The following is a detailed description of the new cultivar as observed on plants about one year in age as grown in 2-gallon containers in Alpharetta, Ga. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Blooms from late May/early June until Frost in Pennsylvania.

*Plant habit*.—Herbaceous perennial, densely clump-forming with numerous basal branching to produce a bushy habit.

*Height and spread*.—Reaches a height of 45 to 60 cm (18 to 24 inches) and an average spread of 45 cm (18 inches).

*Cold hardiness*.—At least in U.S.D.A Zone 5.

*Diseases resistance*.—No particular resistance or susceptibility has been observed.

*Root description*.—Fibrous, fine and well-branched.

Growth and propagation:

*Propagation*.—Terminal stem cuttings.

*Growth rate*.—Vigorous and propagates well under greenhouse conditions in winter.

Stem description:

*Shape*.—Round, solid.

*Stem color*.—143C.

*Stem size*.—An average of 27 cm in length (to the bottom of the inflorescence) and 2 mm in width.

*Stem surface*.—Glabrous, satin finish, slightly ridged.

*Branching habit*.—An average of 70 basal branches with laterals produced with pinching.

Foliage description:

*Leaf division*.—Simple, deeply incised, primarily tri-lobed.

*Leaf margins*.—Entire.

*Leaf size*.—Up to 7 cm in length and 5 cm in width, lobes an average of 6 cm in length and 2 mm in width.

*Leaf shape*.—Fan shaped overall, lobes narrowly linear.

*Leaf base*.—Attenuate.

*Leaf apex*.—Acute.

*Leaf venation*.—Pinnate, not prominent, matches leaf color on both surfaces.

*Leaf attachment*.—Sessile.

*Leaf arrangement*.—Opposite.

*Leaf internode length*.—Average of 5 cm.

*Leaf quantity*.—An average of 10 per stem.

*Leaf surface*.—Glabrous.

*Leaf color*.—Young and mature leaves upper and lower surfaces; 146A.

*Leaf fragrance*.—Faint and slightly sweet when crushed.

Flower description:

*Inflorescence type*.—Composite with ray florets surrounding disk florets in the center forming a radiant head, inflorescences emerge from nodes and terminus.

*Lastingness of inflorescence*.—About one week until senescence of ray flowers, bracts and disk flowers are persistent.

*Fragrance*.—None detected:

*Quantity of inflorescences*.—An average of 7 per stem.

*Inflorescence size*.—An average of 1-cm in depth and up to 4.5 cm in width with disk portion an average of 7 mm in diameter.

*Inflorescence buds*.—Average of 4 mm in depth and 5 mm in width, shape is rounded-oblate, color is 144A with apex 144B.

*Peduncle*.—Average of 6 cm in length and 1 mm in diameter, 143C in color, glabrous surface.

Involucral bracts:

*Bract number*.—Two rows of 8 typically.

*Bract arrangement*.—Outer bracts are un-fused spreading and held at 45° from perpendicular, inner bracts overlap and surround receptacle with a campanulate form and held close to ray florets with apical portion spreading outward.

*Bract size*.—Outer bracts about 2 mm in length and 1 mm in width, inner bracts about 6 mm in length and 2 mm in width with free portion an average of 3 mm in length and 2 mm in width.

*Bract color*.—Outer bracts; 144B with apex 137B and a thin margin of 149D (both surfaces), inner bracts; base 144B with apex 154A (both surfaces).

*Bract texture*.—Outer bracts glabrous and satiny on both surfaces, inner bracts glabrous and waxy on both surfaces.

*Bract apex*.—Acute (inner and outer).

*Bract base*.—Truncate (inner and outer).

*Bract shape*.—Outer bracts narrowly lanceolate, inner bracts broadly lanceolate.

Ray florets (sterile):

*Number*.—Average of 8.

*Shape*.—Elliptic to oblong.

*Size*.—Average of 1.3 cm in length and 5 mm in width.

*Apex*.—Obcordate.

*Base*.—Cuneate.

*Margins*.—Entire.

*Aspect*.—Held nearly horizontal to slightly upward.

*Surface*.—Glabrous and ridged on both surfaces.

*Color*.—Upper surface-opening; 53A, upper surface mature; 53A with flecks (most prominently at apex) of 161B, lower surface opening and mature; 161A and diffused with N34A at base with a very thin margin of N34A.

Disk flowers (male and female):

*Number*.—Numerous, about 80.

*Shape*.—Tubular, corolla is fused, flared at apex.

*Size*.—About 4 mm in length and 1 mm in width.

*Color*.—In masse: 9A, with stigmas 23A, corolla; 14A and apex 149A.

*Receptacle*.—About 3 mm in diameter and 2 mm in depth, 144A in color.

Reproductive organs:

*Presence*.—Disk flowers are perfect, ray flowers are sterile.

*Gynoecium*.—1 Pistil, 4 mm in length, style is very fine and about 11B in color and translucent, bifid pilose stigma is 17A in color with branches about 1 mm in length and recurved, ovary is 0.5 mm in length, inferior, and 11D in color.

*Androcoecium*.—5 stamens, fused into tube surrounding style, 1 mm in length, about 200A in color, no pollen was observed.

*Fruit/seed*.—Seed pods; oblong in shape, slightly curved with narrow wings, about 8.5 mm in length and 3 mm in width, a blend of 199A and 200A in color, seeds; 20 to 30 per pod, about 4.5 mm in length and 1.5 mm in width, 200A in color.

It is claimed:

1. A new and distinct cultivar of *Coreopsis* plant named 'Broad Street' as herein illustrated and described.

* * * * *